(12) United States Patent
Althöfer et al.

(10) Patent No.: US 7,537,383 B2
(45) Date of Patent: May 26, 2009

(54) PROTECTIVE ELEMENT FOR A MEASURING PROBE AND CORRESPONDING MEASURING PROBE, HONEYCOMB BODY AND MOTOR VEHICLE

(75) Inventors: Kait Althöfer, Wiehl (DE); Rolf Brück, Bergisch Gladbach (DE)

(73) Assignee: Emitec Gesellschaft fuer Emissionstechnologie mbH, Lohmar (DE)

( * ) Notice: Subject to any disclaimer, the term of this patent is extended or adjusted under 35 U.S.C. 154(b) by 0 days.

(21) Appl. No.: 11/800,534

(22) Filed: May 7, 2007

(65) Prior Publication Data
US 2007/0242728 A1    Oct. 18, 2007

Related U.S. Application Data

(63) Continuation of application No. PCT/EP2005/011561, filed on Oct. 28, 2005.

(30) Foreign Application Priority Data
Nov. 5, 2004    (DE) ................. 10 2004 053 460

(51) Int. Cl.
*G01K 1/08* (2006.01)
*G01K 1/14* (2006.01)
*G01K 13/02* (2006.01)

(52) U.S. Cl. ............... 374/144; 374/152; 374/208

(58) Field of Classification Search ........... 123/65 PE, 123/676; 73/114.01, 114.34, 114.69, 114.71–114.74, 73/114.77, 73, 23.31, 866.5; 374/163, 164, 374/183, 185, 179, 16
See application file for complete search history.

(56) References Cited

U.S. PATENT DOCUMENTS

| 3,844,920 | A |   | 10/1974 | Burgett et al. |
| 4,157,288 | A | * | 6/1979 | Fleckenstein et al. ....... 204/415 |
| 4,193,499 | A | * | 3/1980 | Lookholder ................ 206/524 |
| 4,347,732 | A |   | 9/1982 | Leary |
| 4,486,553 | A | * | 12/1984 | Wesch ........................ 523/179 |
| 4,745,711 | A |   | 5/1988 | Box |
| 4,857,364 | A | * | 8/1989 | von Bonin ................ 427/254 |
| 5,073,247 | A |   | 12/1991 | Weyl |
| 5,151,110 | A | * | 9/1992 | Bein et al. .................. 95/140 |
| 5,318,504 | A | * | 6/1994 | Edenbaum et al. ............. 602/8 |
| 5,729,988 | A | * | 3/1998 | Tchernev .................... 62/106 |
| 5,948,963 | A |   | 9/1999 | Kato et al. |
| 6,089,014 | A | * | 7/2000 | Day et al. ................... 60/274 |
| 6,276,191 | B1 |  | 8/2001 | Schneider et al. |
| 6,935,099 | B2 |  | 8/2005 | Miyahara et al. |
| 7,033,421 | B1 | * | 4/2006 | Smith et al. .................. 96/135 |

(Continued)

FOREIGN PATENT DOCUMENTS

| DE | 24 52 924 A1 | 6/1975 |
| DE | 37 87 243 T2 | 4/1994 |
| DE | 43 39 737 C1 | 1/1995 |
| DE | 43 25 261 A1 | 2/1995 |
| DE | 196 07 947 C1 | 6/1997 |

(Continued)

*Primary Examiner*—Gail Verbitsky
(74) *Attorney, Agent, or Firm*—Laurence A. Greenberg; Werner H. Stemer; Ralph E. Locher

(57) ABSTRACT

A protective element for a measuring probe, in particular a measuring probe for use in the exhaust system of a motor vehicle, includes at least one temporarily water-binding layer which binds water chemically and/or physically in a first operating state and releases the bound water in a second operating state. A corresponding measuring probe, honeycomb body and motor vehicle are also provided.

40 Claims, 2 Drawing Sheets

U.S. PATENT DOCUMENTS

| | | |
|---|---|---|
| 2002/0011066 A1 | 1/2002 | Takakura et al. |
| 2002/0014107 A1* | 2/2002 | Moos et al. ............... 73/31.05 |
| 2002/0092779 A1* | 7/2002 | Essalik et al. ............... 205/781 |
| 2002/0106307 A1* | 8/2002 | Clyde et al. ................... 422/98 |
| 2002/0122179 A1* | 9/2002 | Pipino ........................ 356/440 |
| 2002/0134995 A1* | 9/2002 | Yan et al. ..................... 257/200 |
| 2003/0062264 A1* | 4/2003 | Kitanoya et al. ............. 204/424 |
| 2003/0121780 A1* | 7/2003 | Dutta et al. .................. 204/424 |
| 2004/0231322 A1 | 11/2004 | Miyahara et al. |
| 2004/0253493 A1* | 12/2004 | Kamijo ........................ 429/20 |
| 2006/0144226 A1* | 7/2006 | Damrath et al. ................ 95/90 |
| 2007/0056352 A1* | 3/2007 | Birkhofer et al. .......... 73/23.21 |
| 2007/0125664 A1* | 6/2007 | LaBarge et al. .......... 205/780.5 |
| 2007/0237206 A1* | 10/2007 | Kubota et al. ............... 374/164 |

FOREIGN PATENT DOCUMENTS

| | | |
|---|---|---|
| DE | 198 32 098 A1 | 1/2000 |
| DE | 198 53 472 A1 | 5/2000 |
| DE | 200 04 514 U1 | 7/2001 |
| DE | 101 25 776 A1 | 12/2002 |
| DE | 103 12 106 B4 | 10/2004 |
| EP | 0 264 097 A2 | 4/1988 |
| EP | 0 880 025 A1 | 11/1998 |
| EP | 1 002 973 A2 | 5/2000 |
| EP | 1 261 052 A2 | 11/2002 |
| EP | 1 422 392 A1 | 5/2004 |
| JP | 05340910 A * | 12/1993 |
| WO | 01/67082 A1 | 9/2001 |

* cited by examiner

PROTECTIVE ELEMENT FOR A MEASURING PROBE AND CORRESPONDING MEASURING PROBE, HONEYCOMB BODY AND MOTOR VEHICLE

CROSS-REFERENCE TO RELATED APPLICATIONS

This is a continuing application, under 35 U.S.C. § 120, of copending International Application No. PCT/EP2005/011561, filed Oct. 28, 2005, which designated the United States; this application also claims the priority, under 35 U.S.C. § 119, of German Patent Application DE 10 2004 053 460.8, filed Nov. 5, 2004; the prior applications are herewith incorporated by reference in their entirety.

BACKGROUND OF THE INVENTION

Field of the Invention

The invention relates to a protective element, in particular for use in the exhaust system of an internal combustion engine for preventing water shock on measuring probes. The invention also relates to a measuring probe having such a protective element, a honeycomb body, in particular a catalyst carrier body and/or filter body with such a measuring probe and a corresponding motor vehicle. The preferred field of application is in the exhaust system of a motor vehicle, for example of an automobile or of a motor-operated two-wheeled vehicle.

Measuring probes, in particular lambda probes, which are used in the exhaust systems of internal combustion engines, for example in honeycomb bodies, are often made inoperative by water shock. Water shock is understood to be the process of wetting of the surface of the measuring probe with fluid water or the condensing out of water vapor on the surface of the measuring probe.

SUMMARY OF THE INVENTION

It is accordingly an object of the invention to provide a protective element for a measuring probe and a corresponding measuring probe, honeycomb body and motor vehicle, which overcome the hereinafore-mentioned disadvantages of the heretofore-known devices of this general type and which reliably prevent a water shock on a measuring probe, since a water shock generally leads to irreparable damage or at least to a malfunction of the measuring probe.

With the foregoing and other objects in view there is provided, in accordance with the invention, a protective element for a measuring probe, especially for use in an exhaust system of a motor vehicle. The protective element comprises at least one temporarily water-binding layer binding water chemically and/or physically in a first operating state and releasing the bound water in a second operating state. The protective element according to the invention is suitable, in particular, for a measuring probe for use in the exhaust system of a motor vehicle. The protective element is preferably configured in such a way that an inner surface can be applied at least partially to an outer surface of the measuring probe.

When a measuring probe is installed in a honeycomb body such as, for example, a catalyst carrier body and/or a filter body, a temperature minimum is also present at the base of the measuring probe, particularly in a cold starting phase of an internal combustion engine, due to the exothermic catalytic reaction. The base lies on the outer surface of the honeycomb body, in particular on an outer casing tube which is provided there. This is due to the maximum thermal capacity which is present there and which brings about relatively slow heating. If the catalytic reaction has then started in parts of the honeycomb body, it is possible for water vapor to form in the interior of the honeycomb body due to the exothermic character of the reaction. If the water vapor then touches the measuring probe, in particular a lambda probe, water condenses out in that case, that is to say a water shock occurs, at the coldest point, in particular on the outer surface of the honeycomb body and/or the base of the measuring probe bearing against the outer casing tube, which base heats up slowly as a result of the relatively high thermal capacity of the outer casing tube at that point. If a protective element according to the invention is then formed there, in particular as an additional component which simply fits snugly over the measuring probe or else is integrally formed onto it, the water-binding layer causes water to be bound temporarily on or in the layer chemically and/or physically by chemisorption or physisorption in the first operating state. In particular, in the case of heated lambda probes, the protective element can also be constructed in such a way that a gap is formed between an inner surface of the protective element and an outer surface of the measuring probe, at least in certain areas. If the measuring probe includes a measuring sensor, which is for example a corresponding semiconductor component that is surrounded by a protective cap which provides in particular protection against mechanical and/or thermal influences on the measuring sensor, the protective element can also preferably be constructed in such a way that it is formed between the measuring sensor and the protective cap.

The present chemical and/or physical bonding is reversible by changing into the second operating state. The change into the second operating state can be carried out, for example, by increasing the temperature so that, for example, water adsorbs onto and/or into the water-binding layer at temperatures below a limiting temperature, and desorbs again after the limiting temperature has been exceeded. The protective element is preferably also formed in its entirety from a temporarily water-binding material so that the temporarily water-binding layer forms the entire protective element.

The water-binding layer thus acts as a type of sponge in which the water that causes the water shock is at least partially temporarily bound. If a large number of cold starts are carried out one after the other without the limiting temperature being exceeded, that would cause the water absorption capacity of the water-binding layer to be exhausted at a specific time. For that reason, an engine management system for the internal combustion engine is particularly advantageous, in particular within the scope of the engine control system of the internal combustion engine of an automobile in which the execution of a plurality of cold starts which do not bring about a change into the second operating state is detected and the composition and/or quantity of the fuel is changed in good time before the water absorption capacity of the water-binding layer is exhausted, with the result that, for example, unburnt hydrocarbons reach the honeycomb body and are burnt there so that the second operating state is reliably brought about.

The suitability of the protective element for a measuring probe for use in the exhaust system of a motor vehicle has the result, in particular, that the protective element can withstand the conditions in the exhaust system, in particular the temperatures present there and the temperature transients and/or temperature gradients occurring there, the corresponding gas pressures and/or highly reactive substances as well as mechanical loading and vibrations or impacts. Depending on the construction of the protective element, it may be suitable for surrounding the measuring probe and/or the measuring sensor completely or else only around part of its circumference, in particular in certain areas. In the latter case, the protective element can be constructed, for example, as a circular ring segment. It is also possible, and in accordance with the invention, to form a plurality of corresponding protective elements which extend around part of the circumference and which together enclose the measuring probe around its entire circumference, in particular in an axial region.

In accordance with another feature of the invention, the protective element has a substantially closed shape with an inner surface and an outer surface, and in particular the protective element is in the form of a ring and/or circular ring.

The protective element may be constructed, in particular, in an annular fashion as a protective ring. A ring designates, in this context, in particular, a closed structure which matches and/or can be matched in its geometric shape to the geometric shape of a measuring probe, a protective cap and/or a measuring sensor. A ring can consequently not only have a circular ring-shaped geometry but rather, for example, can also have the basic shape of a polygon, preferably of a hexagon or quadrilateral, in particular a square or a rectangle or else an ellipse. Any closed, annular structure which has an outer surface and an inner surface is to be considered a ring within the sense of the present invention.

In accordance with a further feature of the securing ring according to the invention, the protective element is at least partially compressible or elastic.

When the protective element is constructed as a component which is separate from the measuring probe, this advantageously facilitates the attachment of the protective element to the measuring probe, for example by making it simply fit snugly over the measuring probe.

In accordance with an added feature of the securing ring according to the invention, at least the temporarily water-binding layer is porous, and has in particular a porosity of at least 40%, preferably more than 70%.

The formation of at least the temporarily water-binding layer as a porous structure advantageously increases the surface which is available for chemical and/or physical binding of the water.

In accordance with an additional feature of the invention, the protective element, in particular the water-binding layer, comprises at least one of the following materials:

a) mica;
b) aluminum oxide, in particular y-aluminum oxide; or
c) zeolite, in particular zeolite A, X and/or Y and/or faujasite.

Mica is understood in particular to be silicate materials which crystallize in a monoclinic fashion, for example muscovite, lepidolite, biotite or paragonite. In particular, mica is understood to be materials, which can be represented by the following formula:

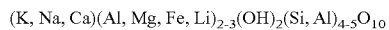

$(K, Na, Ca)(Al, Mg, Fe, Li)_{2-3}(OH)_2(Si, Al)_{4-5}O_{10}$ where the atoms in brackets can be represented in any desired combination. The term zeolite is understood to mean both naturally occurring and synthetically manufactured aluminosilicates, in particular also those which have been subjected to at least partial cationic exchange. Basically however, it is also possible, and in accordance with the invention, to use other materials to construct the water-binding layer if, through the use of these materials, water can be bound in a first operating state and released again in a second operating state. The formation of the water-binding layer from a plurality of materials or a plurality of water-binding layers is also possible and in accordance with the invention.

In accordance with yet another feature of the invention, the protective element is temperature resistant at temperatures up to 500° C., preferably 750° C., particularly preferably 1000° C.

Such temperature resistance advantageously permits use in the exhaust system of an automobile.

In accordance with a further feature of the invention, the first operating state and the second operating state differ in operating temperature.

Accordingly, the change from one operating state to the other can be brought about by changing the operating temperature, that is to say the temperature which is present at the protective element.

In accordance with yet an added feature of the invention, the first operating state is present substantially at temperatures below a limiting temperature, in particular a desorption temperature, and the second operating state is present substantially at temperatures above the limiting temperature.

This distinguishes, in particular, the temporary binding of the water by adsorption. Limiting temperature is to be understood herein also as a limiting temperature range in which a change in the ratio of adsorption to desorption occurs at or in the water-binding layer.

In accordance with yet an additional feature of the invention, the limiting temperature is higher than the boiling temperature of water.

This effectively prevents water from being released by the water-binding layer and condensing directly out again. In particular, the limiting temperature is higher than 100° C.

In accordance with still another feature of the invention, the water-binding layer is located at least partially on a surface of the protective element.

In accordance with still a further feature of the invention, the water-binding layer is formed at least partially on a surface of the protective element which is at least partially on the outside in relation to the measuring probe and/or in relation to a measuring sensor.

The water-binding layer is thus at least not exclusively formed on the inner surface of the protective element and also not exclusively formed on the outer surface of the protective element which in particular bears against the inner surface of the measuring probe wall when the measuring sensor is installed later. This means that the water-binding layer is preferably formed in areas at the surface of the protective element which are in contact with the exhaust gas when the protective element is used, for example, in the honeycomb body.

In accordance with still an added feature of the invention, the protective element is suitable for substantially gas-tight abutment against the outer surface of the measuring probe and/or of the measuring sensor.

In accordance with still an additional feature of the invention, the protective element is suitable for substantially gas-tight abutment against an inner surface of a measuring probe bore.

By virtue of the suitability for substantially gas-tight abutment against the outer surface of the measuring probe and/or the inner surface of the measuring probe bore, the protective element can also carry out a sealing function, and can, for example, be constructed as a sealing ring.

In accordance with again another feature of the invention, the protective element includes a heater or heating device.

The protective element can be heated by such a heater or heating device. Heating the protective element additionally effectively reduces the possibility of water shock. The heater or heating device may, for example, include a simple heating wire which is formed in the interior of the protective element.

With the objects of the invention in view, there is also provided a measuring probe, in particular a lambda probe, a temperature sensor and/or a gas concentration sensor, for an exhaust system of an internal combustion engine. The measuring probe comprises at least one protective element according to the invention.

In accordance with another feature of the measuring probe according to the invention, the measuring probe includes a measuring sensor, and the protective element includes at least an inner surface which abuts at least partially against an outer surface of the measuring probe and/or of the measuring sensor and/or is formed at least partially opposite an outer surface of the measuring probe and/or of the measuring sensor. It is particularly preferred in this case for a gap to be formed between the outer surface of the measuring probe and/or of the measuring sensor and the inner surface of the protective element, at least in certain areas.

In accordance with a further feature of the invention, the protective element can preferably be integrally formed on the measuring probe and/or the measuring sensor and/or be connected thereto in a materially joined fashion, in particular welded thereto. A form-locking and/or force-locking connection is also possible and in accordance with the invention. A form-locking connection is one which connects two elements together due to the shape of the elements themselves, as opposed to a force-locking connection, which locks the elements together by force external to the elements.

In accordance with an added feature of the invention, the measuring probe includes a protective cap. The protective element is formed between the protective cap and the measuring sensor.

A protective cap is generally formed, in particular, on lambda probes. In this case, the protective cap surrounds the measuring sensor, with suitable openings permitting the gas to be analyzed to pass to the measuring senor of the lambda probe which lies inside the protective cap. This protective cap serves primarily to avoid transportation damage and installation damage. Although such a protective cap is also intended to prevent water shock, that is to say for example a thermal shock to the generally heated measuring sensor through contact with water droplets, damage due to water shock occurs relatively often despite such protective caps, in particular if a motor vehicle is predominantly driven over short distances, that is to say generally in cold start phases. In such a case, the provision of the protective element according to the invention additionally between the protective cap and the actual measuring sensor can further significantly reduce the risk of water shock, in particular in the case of lambda probes.

With the objects of the invention in view, there is additionally provided a honeycomb body, in particular a catalyst carrier body and/or filter body. The honeycomb body comprises cavities through which a fluid can flow, and at least one protective element according to the invention and/or at least one measuring probe according to the invention.

The honeycomb body according to the invention may be constructed from metallic and/or ceramic materials, and in particular can be wound or layered and twisted or else extruded from at least partially textured metallic and/or ceramic layers and, if appropriate substantially smooth metallic and/or ceramic layers.

In accordance with another feature of the honeycomb body of the invention, the water-binding layer includes at least partially a surface of the protective element which can be placed in fluid mechanical contact with the cavities.

In fluid mechanical contact means in this context in particular that when a fluid, in particular exhaust gas, flows through the honeycomb body, it can come into contact with or flow around the measuring sensor and/or protective element. In this case, the protective element effectively prevents water shock, in particular if it is provided at the location on the measuring probe with the greatest thermal capacity such as, for example, at a base at the junction between the measuring probe and outer casing tube of the honeycomb body.

With the objects of the invention in view, there is concomitantly provided a motor vehicle, in particular an automobile, a motorized two-wheeled vehicle, an aircraft or a boat. The motor vehicle comprises at least one honeycomb body according to the invention, a measuring probe according to the invention and/or a protective element according to the invention.

Other features which are considered as characteristic for the invention are set forth in the appended claims.

Although the invention is illustrated and described herein as embodied in a protective element for a measuring probe and a corresponding measuring probe, honeycomb body and motor vehicle, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

The details and advantages which are disclosed for the protective element according to the invention can be transferred and applied in the same way to the measuring probe according to the invention, the honeycomb body according to the invention and/or the motor vehicle according to the invention. Further advantages and exemplary embodiments of the invention are explained with reference to the drawing without restricting the invention thereto.

DETAILED DESCRIPTION OF THE INVENTION

Figure 1:
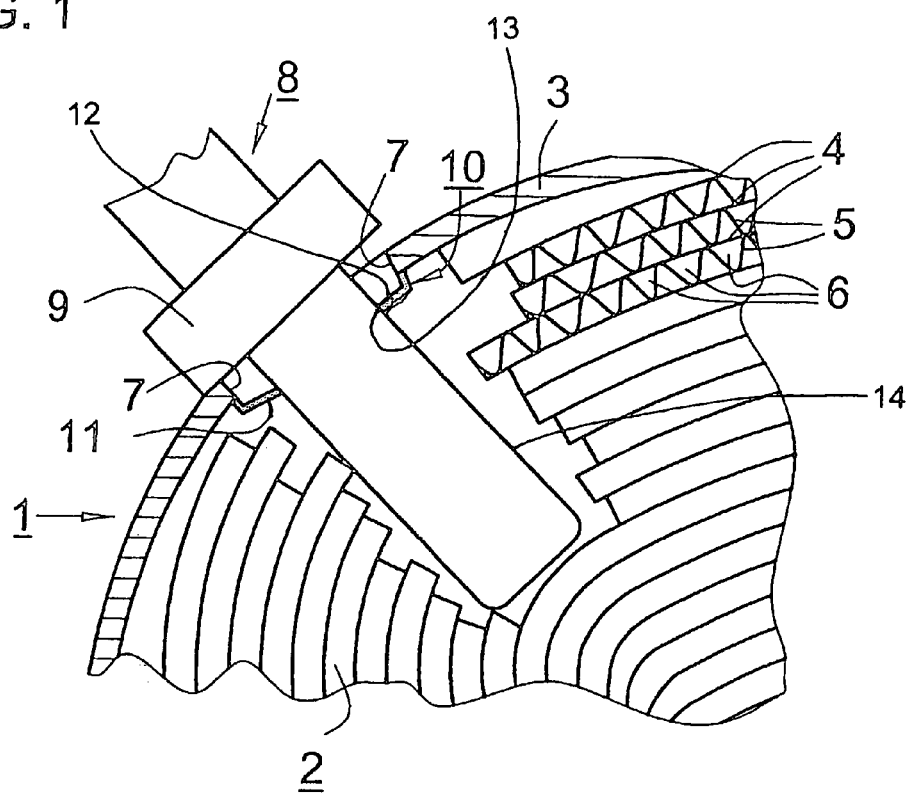
FIG. 1 is a fragmentary, diagrammatic, cross-sectional view of a honeycomb body according to the invention, with a first exemplary embodiment of a protective element according to the invention.

Referring now to the figures of the drawings in detail and first, particularly, to FIG. 1 thereof, there is seen a honeycomb body 1 including a honeycomb structure 2 and a casing tube 3. The honeycomb structure 2 is constructed in the present example by stacking and twisting substantially smooth layers 4 and at least partially structured layers 5 which, for the sake of clarity, are only partially shown. The layers 4, 5 can be constructed from metallic and/or ceramic material, in particular filter material as well. The layers 4, 5 form cavities 6 through which a fluid can flow, in the present example channels which extend from one end of the honeycomb body 1 to the other.

The casing tube 3 has a measuring probe bore 7 in which a measuring probe 8 is placed. A connecting device 9, for example a thread, is formed in order to secure the measuring probe 8 in the measuring probe bore 7. The connecting device 9 corresponds to a matching, non-illustrated connecting device of the measuring probe 8.

A protective element 10 is provided between the measuring probe bore 7 and the measuring probe 8. The protective element 10 has a water-binding layer 11 which is formed on the surface of the protective element 10 in such a way that when the exhaust gas flows through the honeycomb body 1, the protective element 10 comes into contact with the exhaust gas. In this context, the water-binding layer 11 is formed on the outside relative to the measuring probe 8, in particular not on an inner surface 13 of the protective element 10 which is in direct contact with an outer surface 14 of the measuring probe 8. A carrier layer 12 is formed under the water-binding layer 11 and may, for example, be elastic or compressible. However, it is also possible and in accordance with the invention to form the entire protective element 10 as the water-binding layer 11. The provision of the water-binding layer 11, which as stated above permits the temporary chemical and/or physical binding of water, can effectively prevent water shock due to water from water vapor contained in the exhaust gas, in particular in the cold start phase of the engine, condensing out before the honeycomb body 1 has therefore reached a temperature which is above the boiling point of water. In this context, the binding layer 11 acts as a type of sponge which temporarily stores water and releases it again. In the case of a water-binding layer which binds water through absorption, the water can be released through desorption after a desorption temperature has been exceeded if the honeycomb body 1, and thus also the protective element 10 and the water-binding layer 11, become hotter due to heating through exhaust gas and the exothermal reaction which occurs.

Figure 2:
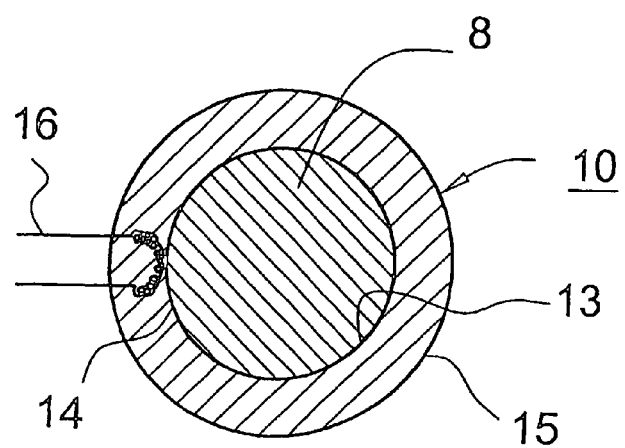
FIG. 2 is a cross-sectional view of a second exemplary embodiment of the protective element according to the invention.

FIG. 2 shows a cross section of a measuring probe 8 with a second exemplary embodiment of a protective element 10 according to the invention. The protective element 10 is constructed in this case as a protective ring which completely surrounds the periphery of the measuring probe 8. An inner surface 13 of the protective element 10 abuts against an outer surface 14 of the measuring probe in a substantially gas-tight fashion. When there is substantially gas-tight abutment of an outer surface 15 of the protective element against a non-illustrated inner surface of a measuring probe bore 7, the protective element 10 at the same time carries out a sealing function in order to effectively prevent exhaust gas from emerging from the honeycomb body 1. Furthermore, a heater or heating device 16 is provided which in the present exemplary embodiment is composed of a heating coil. Other heating devices 16 are possible in accordance with the invention.

Figure 3:
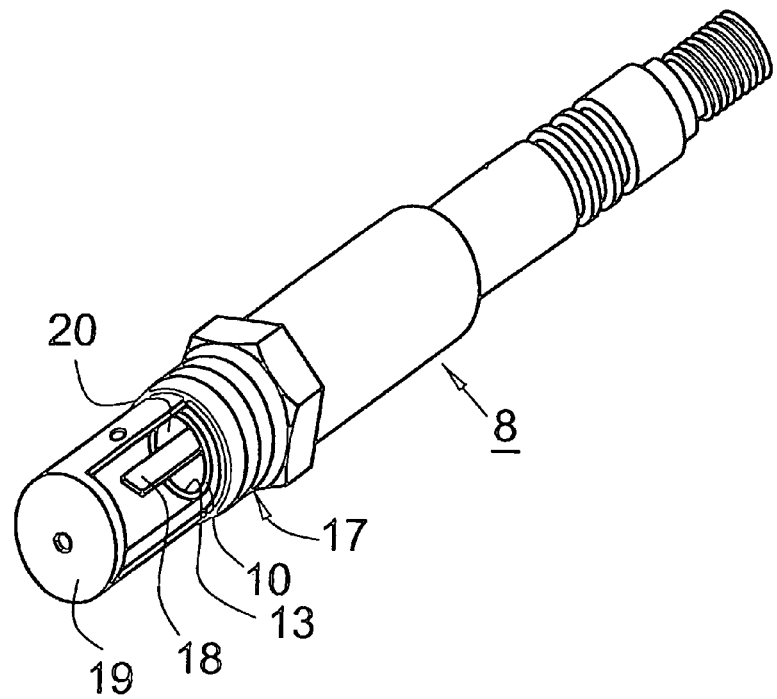
FIG. 3 is a perspective view of a measuring probe according to the invention.

FIG. 3 is a diagrammatic view of a measuring probe 8 according to the invention, which has a thread 17 that corresponds to a connecting device 9 of a measuring probe bore. The actual recording of measured values is carried out in this case through the use of a measuring sensor 18 which is constructed, for example, with a rectangular geometry as a semiconductor component. The measuring sensor 18 is surrounded by a protective cap 19 which, for example, protects the measuring sensor 18 against mechanical effects. The protective element 10 according to the invention is formed in the interior of the protective cap 19 so that a gap 20 is formed between an inner surface 13 of the protective element 10 and an outer surface of the measuring sensor 18. This is advantageous, in particular, if the measuring probe 8 is constructed so as to be heated, in particular in the region of the measuring sensor 18. In such a measuring sensor 18, the protective element 10 serves as an additional protection against possible water shock.

Figure 4:
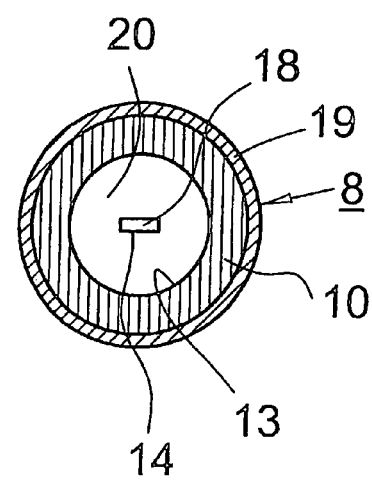
FIG. 4 is a cross-sectional view of a measuring probe according to the invention.

FIG. 4 is a diagrammatic, cross-sectional view of a measuring probe 8 according to the invention, including a measuring sensor 18, a protective cap 19 and a protective element 10 according to the invention. The protective element 10 is constructed in such a way that an inner surface 13 of the protective element 10 is separated from an outer surface 14 of a measuring sensor 18 by a gap 20. In this case, the shape and size of the gap 20 can vary depending on the exemplary embodiment.

The protective element 10 according to the invention effectively prevents water shock on the measuring probe 8 due to the presence of the water-binding layer 11, since water condensing out from water vapor, in particular in the cold start phase, at the point on the measuring probe 8 with the greatest thermal capacity, is prevented. The water-binding layer 11 temporarily binds the water in one operating state in order to release it again in another operating state.

The invention claimed is:

1. In an exhaust system of an internal combustion engine having a measuring probe with a measuring sensor therein, a protective element comprising:
   at least one temporarily water-binding layer disposed in a vicinity of the measuring probe and the measuring sensor, said layer binding water at least one of chemically or physically in a first operating state and releasing the bound water in a second operating state.

2. The protective element according to claim 1, wherein the protective element has a substantially closed shape with an inner surface and an outer surface.

3. The protective element according to claim 2, wherein said substantially closed shape is a ring or a circular ring.

4. The protective element according to claim 1, wherein the protective element is formed of an at least partially compressible or elastic material.

5. The protective element according to claim 1, wherein at least said temporarily water-binding layer is porous.

6. The protective element according to claim 1, wherein at least said temporarily water-binding layer has a porosity of at least 40%.

7. The protective element according to claim 1, wherein at least said temporarily water-binding layer has a porosity of more than 70%.

8. The protective element according to claim 1, wherein the protective element is formed of at least one of the following materials:
   a). mica;
   b). aluminum oxide; or
   c). zeolite.

9. The protective element according to claim 8, wherein said aluminum oxide is y-aluminum oxide.

10. The protective element according to claim 8, wherein said zeolite is at least one material selected from the group consisting of zeolite A, X, Y and faujasite.

11. The protective element according to claim 1, wherein said water-binding layer includes at least one of the following materials:
   a). mica;
   b). aluminum oxide; or
   c). zeolite.

12. The protective element according to claim 11, wherein said aluminum oxide is y-aluminum oxide.

13. The protective element according to claim 11, wherein said zeolite is at least one material selected from the group consisting of zeolite A, X, Y and faujasite.

14. The protective element according to claim 1, wherein the protective element is temperature-resistant at temperatures up to 500° C.

15. The protective element according to claim 1, wherein the protective element is temperature-resistant at temperatures up to 750° C.

16. The protective element according to claim 1, wherein the protective element is temperature-resistant at temperatures up to 1,000° C.

17. The protective element according to claim 1, wherein said first operating state and said second operating state differ in operating temperature.

18. The protective element according to claim 17, wherein said first operating state is present substantially at temperatures below a limiting temperature, and said second operating state is present substantially at temperatures above said limiting temperature.

19. The protective element according to claim 18, wherein said limiting temperature is a desorption temperature.

20. The protective element according to claim 18, wherein said limiting temperature is higher than the boiling temperature of water.

21. The protective element according to claim 1, which further comprises a surface of the protective element, said water-binding layer being located at least partially on said surface.

22. The protective element according to claim 21, which further comprises a surface of the protective element disposed at least partially outwardly relative to the measuring probe, said water-binding layer being formed at least partially on said surface.

23. The protective element according to claim 21, wherein a surface of the protective element is configured to be disposed at least partially outwardly relative to at least one of the measuring probe or said measuring sensor, said water-binding layer being formed at least partially on said surface.

24. The protective element according to claim 1, wherein the protective element is configured for substantially gas-tight abutment against an outer surface of the measuring probe.

25. The protective element according to claim 1, wherein the protective element is configured for substantially gas-tight abutment against one of an outer surface of the measuring probe or an outer surface of the measuring sensor.

26. The protective element according to claim 1, wherein the protective element is configured for substantially gas-tight abutment against an inner surface of a measuring probe bore.

27. The protective element according to claim 1, which further comprises a heater.

28. The protective element according to claim 1, wherein the measuring probe is at least one probe selected from the group consisting of a lambda probe, a temperature sensor and a gas concentration sensor.

29. The protective element according to claim 1, wherein said at least one temporarily water-binding layer has at least an inner surface abutting at least partially against an outer surface of at least one of the measuring probe or of the measuring sensor.

30. The protective element according to claim 1, wherein said at least one temporarily water-binding layer has at least an inner surface disposed at least partially opposite an outer surface of at least one of the measuring probe or the measuring sensor.

31. The protective element according to claim 1, wherein said at least one temporarily water-binding layer has at least an inner surface abutting at least partially against and being disposed at least partially opposite an outer surface of at least one of the measuring probe or of the measuring sensor.

32. The protective element according to claim 1, wherein at least one of the measuring probe or the measuring sensor has an outer surface spaced apart from an inner surface of said temporarily water-binding layer to define a gap therebetween, at least in certain areas.

33. The protective element according to claim 1, wherein said temporarily water-binding layer is at least one of integrally formed on or materially connected to at least one of the measuring probe or of the measuring sensor.

34. The protective element according to claim 1, wherein said temporarily water-binding layer is at least one of force-lockingly or form-lockingly connected to at least one of the measuring probe or of the measuring sensor.

35. The protective element according to claim 1, which further comprises a protective cap, said temporarily water-binding layer is disposed between said protective cap and the measuring sensor.

36. A honeycomb body, comprising cavities through which a fluid can flow, and at least one protective element according to claim 1.

37. The honeycomb body according to claim 36, wherein the honeycomb body is at least one of a catalyst carrier body or a filter body.

38. The honeycomb body according to claim 36, wherein said water-binding layer at least partially includes a surface of said protective element to be placed in fluid mechanical contact with said cavities.

39. A motor vehicle, comprising at least one honeycomb body according to claim 36.

40. The motor vehicle according to claim 39, wherein the motor vehicle is selected from the group consisting of an automobile, a motorcycle, an aircraft and a boat.

* * * * *